United States Patent [19]

Fisher et al.

[11] Patent Number: 5,658,554
[45] Date of Patent: Aug. 19, 1997

[54] MOUTH MOISTENER FOR THE RELIEF OF DRY MOUTH CONDITION

[75] Inventors: Steven W. Fisher, Middlesex; Edward A. Tavss, Kendall Park; Shannon K. Campbell, Piscataway; Marilou T. Joziak, South River; Karen J. De Pierro, Piscataway; John P. Curtis, Bloomsbury, all of N.J.

[73] Assignee: Colgate-Palmolive Company, New York, N.Y.

[21] Appl. No.: 456,586

[22] Filed: Jun. 1, 1995

[51] Int. Cl.⁶ .................................................. A61K 6/00
[52] U.S. Cl. .............................. 424/57; 424/49; 424/52
[58] Field of Search .............................. 424/401, 49, 52, 424/57

[56] References Cited

U.S. PATENT DOCUMENTS

| | | | |
|---|---|---|---|
| 4,820,506 | 4/1989 | Kleinberg et al. | 424/401 |
| 5,208,009 | 5/1993 | Gaffar et al. | 424/49 |
| 5,256,401 | 10/1993 | Duckenfield et al. | 424/49 |

OTHER PUBLICATIONS

Matsumoto et al., *Chemical Abstracts*, vol. 119, 1992, #56260.

Primary Examiner—Jyothsan Venkat
Attorney, Agent, or Firm—Paul Shapiro

[57] ABSTRACT

A mouth moistener for alleviating dry mouth condition comprised of an aqueous vehicle containing less than about 2% by weight an edible organic acid such as citric or malic acid and a mixture of a water soluble calcium ion releasing salt and a water soluble phosphate ion releasing salt, wherein the solution is unsaturated with respect to calcium phosphate and the solubility product (S.P.) of the calcium and phosphate ion concentration present in the solution, as expressed by the equation $$S.P. = [Ca][PO_4]^2$$

is less than about 0.004, wherein [Ca] is the molar concentration of the released calcium ions and [PO₄] is the molar concentration of the released phosphate ion.

16 Claims, No Drawings

MOUTH MOISTENER FOR THE RELIEF OF DRY MOUTH CONDITION

BACKGROUND OF THE INVENTION

1. Field of Invention

This invention relates to a mouth moistener to relieve the symptoms of dry mouth condition and more particularly, to a mouth moistener which is storage stable and relieves dry mouth condition without damage to tooth enamel.

2. Prior Art

Dry mouth is a subjective clinical symptom characterized by a less than a normal amount of saliva with no apparent boundary between normal and abnormal. Dry mouth condition occurs in all age groups and is brought about by numerous reasons, including advancing age, drug, alcohol and nicotine abuse and as side effects in the use of many commonly used prescription medicines such as anti-depressants, antihypertensives and anti-histamines among others.

Various therapeutic measures have been recommended for patients experiencing dry mouth. Some of these include frequent rinsing with saline solutions to keep oral tissue moist and healthy. A second approach is the use of various agents to promote salivation. For example, U.S. Pat. No. 4,820,506 discloses an aqueous composition to stimulate salivation to relieve the symptoms of xerostomia wherein the composition is an acidic (pH 3-4) water solution having dissolved therein 2-3% of a food grade acidulent such as citric acid or malic acid. Because repeated use of acidic solutions is potentially harmful to human teeth and can cause demineralization of tooth enamel, the solution is saturated with calcium phosphate to inhibit damage to tooth enamel. It has now been determined that the inhibition of demineralization afforded by the presence of saturated calcium phosphate in solutions containing citric acid is only temporary, as the calcium phosphate is supersaturated with respect to a less soluble calcium citrate which forms in the solution during storage and precipitates therefrom. The precipitation of calcium citrate leaves the solution undersaturated with respect to calcium phosphate and the demineralization inhibition effect of the phosphate salt is as a consequence substantially diminished. Further, the presence of the calcium citrate precipitate in the solution renders the product aesthetically unappealing as well as causing malfunctioning and clogging of the spray pump systems used to apply the product to the oral cavity for relief of dry mouth condition. In addition, the acidic solution disclosed in U.S. Pat. No. 4,820,506 has been found to impart an unpleasant, pronounced sour or tart taste due to the presence of the relatively high concentration of organic acid making the product unsuitable for use as a mouth moistener.

Therefore, there is a need in the art for mouth moistener which is storage stable, has a less pronounced sour taste and with repeated use is without diminished effect for protecting the tooth enamel of the user.

SUMMARY OF THE INVENTION

In accordance with the practice of the present invention there is provided an aqueous mouth moistener composition for the relief of dry mouth condition which is chemically and cosmetically stable and benign to tooth enamel wherein the composition is comprised of an orally acceptable aqueous solution containing dissolved therein about 0.75% to less than 2% by weight of a an edible organic acid and a mixture of a water soluble calcium ion releasing salt and a water soluble phosphate ion releasing salt, wherein the solution is unsaturated with respect to calcium phosphate and the solubility product (S.P.) of the calcium and phosphate ion concentrations present in the solution, as expressed by the equation $$S.P. = [Ca][PO_4]^2$$

is less than about 0.004, where [Ca] is the molar concentration of the released calcium ions and [PO$_4$] is the molar concentration of the released phosphate ions.

Phosphate ions represented by [PO$_4$] in the equation include [H$_2$PO$_4^{-1}$] monobasic phosphate, [HPO$_4^{-2}$] dibasic phosphate, and [PO$_4^{-3}$] tribasic phosphate.

Although the mouth moistener of the present invention is acidic, it is benign to tooth enamel and has an acceptable taste. The mouth moistener composition of the present invention is chemically and cosmetically acceptable for commercial use. On extended storage very little, if any, precipitate formation is observed in the product.

DESCRIPTION OF THE PREFERRED EMBODIMENTS

The orally acceptable vehicle used to prepare the mouth moistener of the present invention generally includes water, humectant and a thickener.

Illustrative examples of humectants useful in the preparation of the composition of the present invention include glycerol, sorbitol, polyethylene glycol, and xylitol which is most preferred. The humectant will generally be incorporated in the mouth moistener of the present invention in the range of about 1.0 to about 10% by weight and preferably about 3 to about 8% by weight.

Thickeners included in the compositions of the present invention include natural and synthetic gums and colloids such as carrageenan, xanthan gum and sodium carboxymethyl cellulose, as well as gum tragacanth, starch, hydroxyethyl propylcellulose, hydroxybutyl methyl cellulose, hydroxypropyl methyl cellulose and hydroxyethyl cellulose. The thickener component of the composition of the present invention will generally be in the range of 0.01 to 0.10% by weight and preferably 0.03 to 0.08% by weight.

The amount of water included in the mouth moistener composition of the present invention generally ranges from about 80 to about 90% by weight.

In preparing the mouth moistener composition of the present invention, the edible acid constitutes less than about 2% by weight of the composition and preferably about 1.25 to about 1.75% by weight of the composition. Suitable edible organic acids include citric acid, malic acid and mixtures thereof. A mixture of citric acid and malic acid at a weight ratio of about 1:1 is preferred in the practice of the present invention.

Water soluble calcium ion releasing compounds in the form of their acid salt such as calcium chloride are incorporated in the composition of the present invention at a concentration of about 1.25 to about 1.5% by weight. Water soluble phosphate ion releasing compounds are present in the composition of the present invention in the form of their alkali metal salt such as sodium or potassium phosphate such as sodium monobasic phosphate, sodium diabasic phosphate and potassium tribasic phosphate and are incorporated in the composition of the present invention at a concentration of about 1.25 to about 1.75% by weight. By using amounts of released calcium ion and released phosphate ion in the mouth moistener solution of the present invention wherein the solubility product of these ions in accordance with the previously discussed solubility product equation is less than about 0.004, precipitate formation in the mouth moisturizer solution on storage is substantially avoided. Preferably the solubility product of calcium ions and phosphate ions present in the mouth moistener solution of the present invention is about 0.0015 to about 0.0035 and most preferably about 0.002 to about 0.0025 as determined in accordance with the previously discussed equation.

A water soluble fluoride ion source is incorporated in the mouth moisturizer composition of the present invention to inhibit demineralization of tooth enamel by glycolysis of dietary carbohydrates which fluoride ion source provides about 0.5 to about 100 ppm fluoride ion, although higher concentrations may be used. Preferably about 1 to about 10 ppm fluoride ion is incorporated in the mouth moisturizer of the present invention. Sources of fluoride ions include water soluble alkali metal fluorides, such as sodium and potassium fluorides and sodium and potassium monofluorophosphates.

The pH of the mouth moisturizer composition of the present invention is adjusted to a range of 3 to 4 with an alkali metal hydroxide such as sodium hydroxide or potassium hydroxide.

Other adjuvants may be incorporated in the mouth moisturizer composition of the present invention including preservatives such as sodium benzoate, synthetic sweeteners such as acesulfame potassium and sodium saccharin as well as additional salts such as magnesium chloride or potassium chloride to match the electrolyte levels in human saliva.

Various other agents may be included in the mouth moisturizer of the present invention. Included in this group are: anti-tartar compounds such as sodium pyrophosphate, antibacterial agents such as Triclosan, chlorhexidene, cetyl pyridinium chloride and sanguinaria, flavors, such as peppermint, lemon, spearmint and menthol; dyes such as chlorophyll, and surfactants such as nonionic surface active agents such as polyoxyethylene sorbitan monoleate (Polysorbate 20).

To prepare the mouth moistener composition of the present invention, the active ingredients are generally dissolved or dispersed in the orally acceptable vehicle and the pH adjusted to between about 3 to about 4 with a base such as sodium hydroxide or potassium hydroxide.

In relieving dry mouth condition with the mouth moistener composition of the present invention a preferred method of application is by the use of an atomized hand held spray which delivers about 0.12 ml of the composition per actuation.

The following Example is given to illustrate the invention and is not to be considered as limiting the scope of the claims. Unless otherwise indicated all parts and percentages are by weight and all temperatures are in ° F.

EXAMPLE I

Three mouth moisturizer compositions were prepared having the following compositions:

| COMPOSITION INGREDIENTS | A | B | C |
|---|---|---|---|
| | Weight Percent | | |
| Deionized Water | 88.4485 | 87.4485 | 86.4508 |
| Xylitol | 6.0000 | 6.0000 | 6.0000 |
| Sodium Phosphate Monobasic | 1.5000 | 3.1000 | 3.1000 |
| Calcium Chloride-USP | 1.4000 | 0.7500 | 1.4000 |
| Citric Acid | 0.7500 | 0.7500 | 0.7500 |
| Malic Acid | 0.7500 | 0.7500 | 0.7500 |
| Sodium Hydroxide (50% Sol.) | 0.7500 | 0.7500 | 0.7500 |
| Sodium Benzoate | 0.1000 | 0.1000 | 0.1000 |
| Acesulfame Potassium | 0.1000 | 0.1000 | 0.1000 |
| Flavor (Lemon) | 0.1000 | 0.1000 | 0.1000 |
| Hydroxyethylcellulose | 0.0500 | 0.0500 | 0.0500 |

-continued

| COMPOSITION INGREDIENTS | A | B | C |
|---|---|---|---|
| | Weight Percent | | |
| Polysorbate 20 | 0.0500 | 0.0500 | 0.0500 |
| Sodium Monofluorophosphate | 0.0015 | 0.0015 | 0.0015 |
| [Ca] Molarity | 0.126 | 0.067 | 0.126 |
| [POp$_4$] Molarity | 0.125 | 0.258 | 0.258 |
| Solubility Product | 0.0019 | 0.0044 | 0.0084 |

Compositions A, B and C were made by dissolving the calcium chloride, sodium phosphate, citric acid, malic acid and sodium monofluorophosphate in a vehicle mixture containing the water, xylitol, hydroxyethylcellulose, acesulfame potassium, Polysorbate 20 and flavor ingredients at room temperature. The pH of the compositions were adjusted to 3.5 with sodium hydroxide. A clear solution was obtained in each composition. Storage in high density polyethylene bottles at 105° F. for 12 weeks indicated little or no separation or precipitation of the ingredients of Composition A. By way of contrast, an unsightly precipitate first appeared in Composition B within 8 weeks of storage at 105° F. and at the end of the 12 week period increased to an unacceptable limit. By way of further contrast, an unsightly precipitate first appeared in Composition C within 4 weeks of storage at 105° F. and at the end of the 12 week period increased to an unacceptable limit.

EXAMPLE II

To determine whether any damaging effect on human tooth enamel would occur with the use of Composition A of Example I, an in-vitro study was performed using four human teeth placed in a beaker containing 20 milliliters of the mouth moistener solution and the beaker stored in the water bath for three days at 37° C. The pH of the solution was measured at the end of the three day period. The pH of the solution was also measured without the presence of human teeth over the three day period in the water bath. A change (rise) in pH between the solution in which the teeth were present as compared to the solution in which the teeth were not present indicates that demineralization of the enamel has occurred.

The greater the change (rise) in pH determined in a contact solution, the greater the demineralization effect of the solution. The change in pH of Composition A without and without exposure to teeth is recorded in the Table below.

For purposes of contrast, the procedure of Example II was repeated except a 1.5% by weight solution of citric acid designated Composition "D" and a commercial cola carbonated soft drink designated Composition "E" were substituted for Composition A. The pH rise recorded for the comparative Compositions D and E is also recorded in the Table below. Water was used as a control.

| Composition Tested | A | D | E | Control |
|---|---|---|---|---|
| Without Teeth | 3.62 | 2.20 | 2.53 | 7.87 |
| With Teeth | 3.67 | 3.25 | 4.20 | 7.79 |
| pH Change | 0.08 | 1.05 | 1.67 | −0.08 |

The pH data recorded in the Table indicate that Composition A exhibited an insignificant pH change as well as a substantially less demineralization effect on human teeth when compared to either a 1.5% solution of citric acid (Composition D) or a commercial carbonated soft drink (Composition E).

What is claimed is:

1. A mouth moistener composition for alleviating the symptoms of dry mouth condition without significant damage to tooth enamel, the composition comprising an orally acceptable aqueous solution containing about 0.75 to about 1.75 by weight of an edible organic acid selected from the group consistintgt of citric acid, malic acid, and mixtures there of and a mixture of a water soluble calcium ion releasing salt and a water soluble phosphate ion releasing salt, wherein the solution is unsaturated with respect to calcium phosphate and the solubility product (S.P.) of the calcium and phosphate ions present in the solution, as expressed by the equation $$S.P.=[Ca][PO_4]^2$$

is about 0.0015 to about 0.0035 , wherein [Ca] is the molar concentration of the released calcium ions and [$PO_4$] is the molar concentration of the released phosphate ions.

2. The composition of claim 1 wherein the edible organic acid is a mixture of citric acid and malic acid.

3. The composition of claim 1 wherein the solubility product of released calcium ions and released phosphate ions is about 0.002 to about 0.0025.

4. The composition of claim 1 wherein the calcium ion is released by calcium chloride.

5. The composition of claim 1 wherein the phosphate ion is released by sodium monobasic phosphate.

6. The composition of claim 1 wherein the edible organic acid is a mixture of citric acid and malic acid.

7. The composition of claim 6 wherein the citric and malic acids are present in the composition at a weight ratio of about 1:1.

8. The composition of claim 1 wherein the pH is about 3 to about 4.

9. The composition of claim 1 wherein fluoride ion is present in the composition at a concentration of about 0.5 to about 100 ppm.

10. A method for alleviating the symptoms of dry mouth condition without significant damage to teeth in the oral cavity which comprises preparing a composition comprising an orally acceptable aqueous solution containing about 0.75 to about 1.75 by weight of an edible organic acid selected from the group consisting of critic acid, malic acid, and mixtures there of and a mixture of a water soluble calcium ion releasing salt and a water soluble phosphate ion releasing salt, wherein the solution is unsaturated with respect to calcium phosphate and the solubility product (S.P.) of the calcium and phosphate ion concentrations present in the solution, as expressed by the equation $$S.P.=[Ca][PO_4]^2$$

is about 0.0015 to about 0.0035 wherein [Ca] is the molar concentration of the released calcium ions and [$PO_4$] is the molar concentration of the released phosphate ions, the amount of released mixed ions being effective to inhibit demineralization of tooth enamel, and then applying the composition to the oral cavity of a patient suffering from dry mouth condition without the patient encountering significant tooth enamel damage.

11. The method of claim 10 wherein the molar ratio of released calcium ions to released phosphate ions is about 0.002 to about 0.0025.

12. A method of claim 10 wherein the calcium ion is released by calcium chloride.

13. The method of claim 10 wherein the phosphate ion is released by sodium monobasic phosphate.

14. The method of claim 10 wherein the edible organic acid is mixture of citric acid and malic acid.

15. The method of claim 14 wherein the mixture of citric acid and malic acid is present in the composition at a weight ratio of about 1:1.

16. The method of claim 10 wherein fluoride ion is present in the composition at a concentration of about 0.5 to about 1 00 ppm.

* * * * *